United States Patent
Wang et al.

(10) Patent No.: US 7,298,488 B2
(45) Date of Patent: Nov. 20, 2007

(54) SURFACE-PLASMON-RESONANCE SENSING TECHNIQUE USING ELECTRO-OPTIC MODULATION

(75) Inventors: Tzyy-Jiann Wang, Banciao (TW); Wen-Shao Lin, Douliou (TW)

(73) Assignee: National Taipei University of Technology, Taipei (TW)

( * ) Notice: Subject to any disclaimer, the term of this patent is extended or adjusted under 35 U.S.C. 154(b) by 61 days.

(21) Appl. No.: 11/229,627

(22) Filed: Sep. 20, 2005

(65) Prior Publication Data

US 2007/0064235 A1   Mar. 22, 2007

(51) Int. Cl.
   *G01N 21/55* (2006.01)
(52) U.S. Cl. ...................................... 356/445
(58) Field of Classification Search .................. 356/445
   See application file for complete search history.

(56) References Cited

U.S. PATENT DOCUMENTS

| | | | | |
|---|---|---|---|---|
| 4,778,234 A * | 10/1988 | Papuchon et al. | ........... | 385/132 |
| 4,915,482 A * | 4/1990 | Collins et al. | ............... | 359/276 |
| 6,111,248 A * | 8/2000 | Melendez et al. | ........... | 250/239 |
| 6,469,785 B1 * | 10/2002 | Duveneck et al. | ........... | 356/244 |
| 6,485,905 B2 * | 11/2002 | Hefti | ............................ | 435/6 |
| 6,801,691 B2 * | 10/2004 | Berini | .......................... | 385/39 |
| 6,899,849 B2 * | 5/2005 | Meinhart et al. | ......... | 422/82.09 |
| 7,057,786 B2 * | 6/2006 | Sawin et al. | ................. | 359/245 |
| 2002/0031838 A1 * | 3/2002 | Meinhart et al. | ........... | 436/514 |
| 2003/0059147 A1 * | 3/2003 | Berini | ............................ | 385/2 |
| 2004/0081384 A1 * | 4/2004 | Datesman et al. | ............ | 385/12 |
| 2005/0248830 A1 * | 11/2005 | Sawin et al. | ................. | 359/321 |
| 2005/0270538 A1 * | 12/2005 | Meehan et al. | ............. | 356/445 |
| 2006/0173352 A1 * | 8/2006 | Lilge et al. | .................. | 600/476 |
| 2007/0003994 A1 * | 1/2007 | Simpson et al. | .............. | 435/25 |
| 2007/0015151 A1 * | 1/2007 | Schrenzel et al. | ............. | 435/6 |

OTHER PUBLICATIONS

Discrete Least-Squares Approximation, pp. 426-428.
Simple Linear Regression-I, pp. 531-559.

* cited by examiner

*Primary Examiner*—Tarifur Chowdhury
*Assistant Examiner*—Jonathon D Cook
(74) *Attorney, Agent, or Firm*—Dykema Gossett PLLC

(57) ABSTRACT

The present invention provides a sensing method and device based on sensing surface plasmon resonance which can be controlled by the electro-optical modulation. In the case of an integrated-optic device according to the present invention, a voltage is applied on an electro-optical crystal substrate surface with waveguides to modulate the surface plasmon resonance condition on the sensing waveguide. Concentrations of chemicals or bio-chemicals contained in a sample placed on the sensing waveguide can be determined by measuring the dependence of the output light intensity on the applied voltage. Because spectrometer is not needed for measuring the surface plasmon resonance wavelength, drawbacks of conventional integrated-optic surface plasmon resonance sensors, like limited sensitivity, high cost and restrictions on circumstances for measuring, are avoided. The present invention can be applied for real-time dynamic analyses on sample's changes. Therefore, it can be extensively applied in the fields associated with tests of chemical gases and various solutions, pollution monitoring and biochips etc.

10 Claims, 2 Drawing Sheets

SURFACE-PLASMON-RESONANCE SENSING TECHNIQUE USING ELECTRO-OPTIC MODULATION

BACKGROUND OF THE INVENTION

1. Field of the Invention

The present invention relates to a sensing method and device based on the surface plasmon resonance techniques, particularly to a sensing method using the electro-optical modulation to detect surface plasmon resonance. It can be used to determine the concentrations of bio-chemical materials in a sample. Its application includes the following detections, such as determining the concentrations of a medicine, characterizing affinity of a medicine with human serum albumin, monitoring chemicals and environmental pollution, and elsewhere.

2. Description of the Prior Art

Free charges in metal can be driven to move back and forth by an alternating electromagnetic field. The driven changing charge density leads to the so-called plasma oscillation. An electromagnetic wave incident on the metal can couple with the plasmon oscillation to produce the surface plasmon resonance, provided that proper conditions related with the polarization and the wavelength of the incident electromagnetic field are fulfilled. The resonance conditions relate to the conservation of energy and momentum in the system involving the exciting photons and the excited surface plasmons. Since the resonance conditions depend on the dielectric constants of the two materials on two sides of the metal, monitoring the dependence of the energy loss of the electromagnetic wave on the wavelength can be used to determine the dielectric constants. Specifically, the wavelength corresponding to the maximum energy loss is the surface-plasmon-resonance wavelength and can be used to determine the dielectric constants.

The surface plasmon resonance phenomenon as described above is taken as a characterization principle in a surface-plasmon-resonance sensing device, which is usually applied in characterization systems for biological and bio-chemical purposes. This kind of surface plasmon resonance device has the following advantages, such as real-time and/or specific analyzing without a labeling step, high sensitivity, and high throughput screening. Application of this technique can provides real-time characterization of the changes of a sample with the time. Its application fields include the characterization of various chemical gases or solutions, the monitoring of pollution, and the chip design for biological purposes. Furthermore, the integrated-optic version of surface plasmon resonance sensing device exhibits advantages of a solid structure, a small volume, a high sensitivity and portability. It can be further integrated with other integrated-optic devices on a single chip to form an integrated-optic circuit with a variety of functions.

For detecting the dependence of the surface plasmon resonance phenomena on the changes of a sample's properties, a spectrometer is needed in a conventional integrated-optic sensing device based on surface plasmon resonance. The sensitivity of the characterization is limited to the resolution of the spectrometer. For preventing from errors resulting from the vibration of the spectrometer, a vibration isolator for installing the spectrometer is needed. Because of using the spectrometer, the cost for building the characterization system is high. Besides, due to the huge volume of the overall system, its application is limited to laboratory work and not suitable for outdoor real-time sensing.

SUMMARY OF THE INVENTION

The present invention is dedicated to solving the problems of the conventional integrated-optic sensing technique based on surface plasmon resonance described above, such as limited sensitivity, high cost and restricted sensing conditions. The present invention discloses a sensing method and device utilizing the electro-optical modulation. Said sensing method comprises: (1) determining a function describing the electro-optical modulation effect in terms of measuring output intensity versus said applied voltage; (2) determining the slope of regression straight line according to said function describing the electro-optical modulation effect; (3) determining material properties of the sample and/or concentrations therein based on said slope of regression straight line. The presented sensing device comprises: a waveguide region being provided on one side of said substrate, said waveguide region comprising a sensing and a reference waveguide, an input end and an output end, said sensing waveguide being covered by a metallic layer; an electrode section, providing an applied voltage across two sides of said sensing waveguide.

In the present invention, the condition for the surface plasmon resonance is modified by an applied voltage due to the electro-optical effect. The wave intensity is measured at the output end of the waveguide region. Based on the measured changes of the wave intensity in dependence of the applied voltage, the related properties of the sample positioned neighboring to the sensing waveguide, such as concentrations of bio-chemical materials, can be determined.

BRIEF DESCRIPTION OF THE DRAWINGS

The structure and the technical means adopted by the present invention can be best understood by referring to the following detailed description of the preferred embodiments and the accompanying drawings, wherein.

DESCRIPTION OF MAIN COMPONENTS

Figure 1:
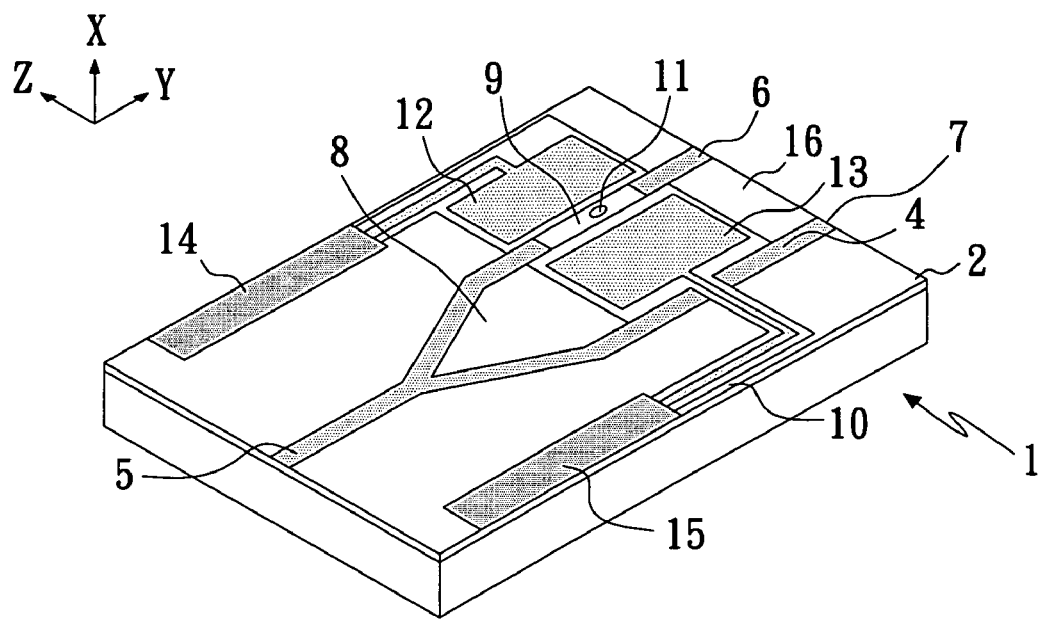
FIG. 1 shows schematically a sensing device of the present invention.

1 X-cut substrate
2 substrate surface
3 sensing waveguide
4 reference waveguide
5 input end
6 sensing output end
7 reference output end
8 bisection of the waveguide region
9 metallic layer
10 separating layer
11 sample
12 electrode end
13 electrode end 14 electrode input end
15 electrode input end
16 isolating layer

DETAILED DESCRIPTION OF THE INVENTION

Figure 2:
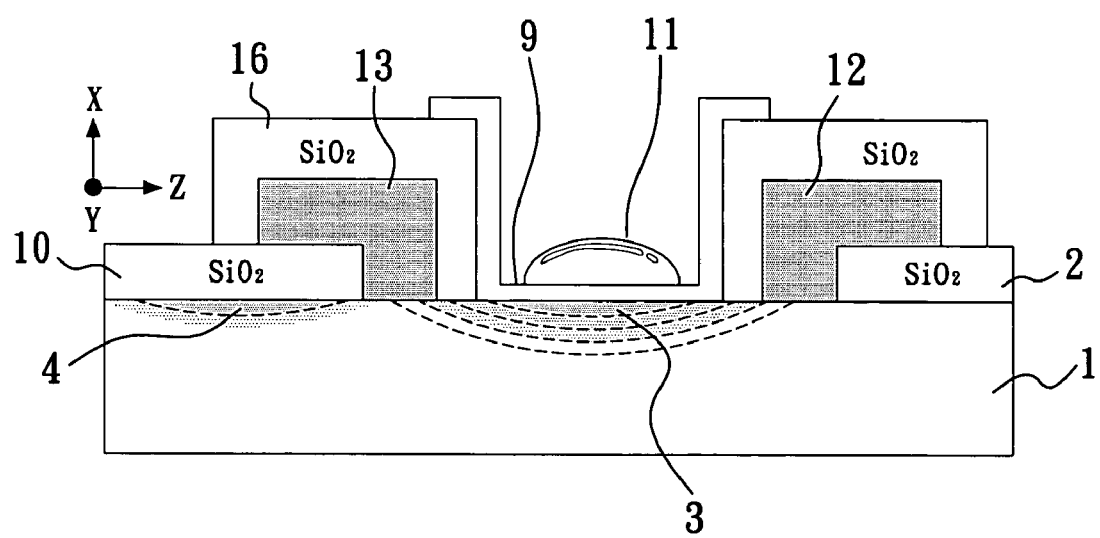
FIG. 2 shows schematically, in cross section, the sensing waveguide in the sensing device of the present invention, viewed along the minus Y-direction.

As shown in FIG. 1 and FIG. 2, a surface-plasmon-resonance sensing device based on the electro-optical effect of the present invention, provided on a substrate 1 with a surface 2, comprises a waveguide region consisting of a sensing waveguide 3 and a reference waveguide 4, and an electrode section with two electrode ends 12, 13 and two electrode input ends 14, 15. The substrate 1 is an X-cut lithium niobate crystal with the X-cut surface 2 which exhibits excellent electro-optical effect. Both the sensing waveguide 3 and the reference waveguide 4 are formed through localized in-diffusion of titanium ions across the substrate surface 2 into the lithium niobate crystal. Other ions, such as zinc and nickel, also can be used to produce the required waveguide in the lithium niobate crystal. Electromagnetic waves transmit essentially along a waveguide direction which is parallel to the Y-direction of the lithium niobate crystal. The sensing waveguide 3 and the reference waveguide 4 share an input end 5 as a common input end for coupling the input electromagnetic wave from a source (not shown) into the sensing waveguide 3 and the reference waveguide 4. A sensing output end 6 and a reference output end 7 for outputting a sensing wave and a reference wave respectively are provided at the other ends of the sensing waveguide 3 and the reference waveguide 4. As exaggeratedly shown in FIG. 1, the waveguide region comprises a bisection 8 with a branching half-angle of about 0.5 degree at the convergent location of the sensing waveguide 3 and the reference waveguide 4. The sensing waveguide 3 is covered by a metallic layer 9 of gold with a thickness of about 30 nm. The material of the metallic layer 9 is not limited and the metals, such as silver and aluminum, can be used. What matters is that free electrons in the metallic layer 9 can be coupled with an electromagnetic wave transmitting in the sensing waveguide 3 to excite surface plasmons. In order to reduce the interference of an sample 11 positioned above the sensing waveguide 3 on the reference waveguide 4, the waveguide region is covered by a separating layer 10 of silicon dioxide which has an opening at the location directly neighboring to the sensing waveguide 3. Furthermore, a voltage can be applied across the two sides of the sensing waveguide 3 through the electrode input ends 14, 15 that connect with the electrode ends 12, 13. The electrode ends 12, 13 are covered by an isolating layer 16 of silicon dioxide with an opening on the sensing waveguide 3, so as to prevent from a direct conducting link between the electrode ends 12 and 13 when a voltage is applied.

As described above and shown in FIG. 1 and FIG. 2, with a sensing device based on the electro-optical effect in the present invention, a sample 11 is positioned on the sensing waveguide 3, and a voltage is applied to the electrode ends 14, 15. The applied voltage produces an electric field along the Z-direction of the X-cut surface 2 on the substrate 1 in the sensing waveguide 3. Due to the electro-optical effect, this electric field leads to changes of the dielectric constant of the sensing waveguide 3. Therefore, tuning the applied voltage will modify the conditions of the surface plasmon resonance, i.e. the wave absorption in metallic layer 9 on the sensing waveguide 3 due to the surface plasmon resonance, and the output intensity at the sensing output end 6. Further, this absorption depends on the applied voltage and the dielectric constant of the sample 11, so that measuring changes of the output intensity at the sensing output end 6 in dependence of the applied voltage will give information about properties of a sample related with the dielectric constant, e.g. concentrations of bio-chemical materials in a solution.

It is to be understood that, in the present invention, the materials of the substrate, the waveguide region, and electrode and the fabrication process are not restricted. Furthermore, the substrate surface on which the waveguides are provided and the waveguide direction are not restricted in relation to the crystalline lattice of the substrate.

In the following, the sensing method of the present invention is explained with an application example of the present invention implemented by the integrated-optic sensing device described above, which is to be applied to measure concentrations of bio-chemical materials.

Figure 3:
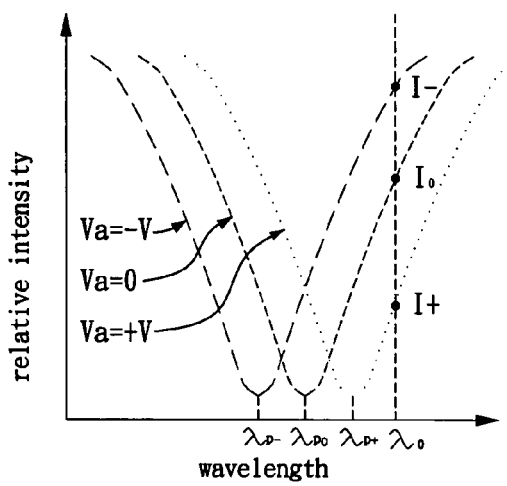
FIG. 3 shows schematically the relative intensity as functions of the wavelength under different applied voltage.

As shown in FIG. 2, a sample 11 is positioned on the sensing waveguide 3, a source device (not shown) is used to generate an input wave, being coupled into input end 5 of the waveguide region e.g. by connecting with an optic fiber. A sensing output intensity and a reference output intensity are measured respectively at the sensing output end 6 and the reference output end 7 by using detectors (not shown). A relative intensity is determined by dividing the sensing output intensity by the reference output intensity, wherein the applied voltage is changed to modify the condition of the surface plasmon resonance, resulting in a function describing the electro-optical modulation effect in terms of the relative intensity as measured output intensity versus the applied voltage. When a white light is used as the input wave, as shown in FIG. 3, every one of the curves of the relative intensity exhibits a minimum due to a characteristic absorption associated with the surface plasmon resonance.

Figure 4:
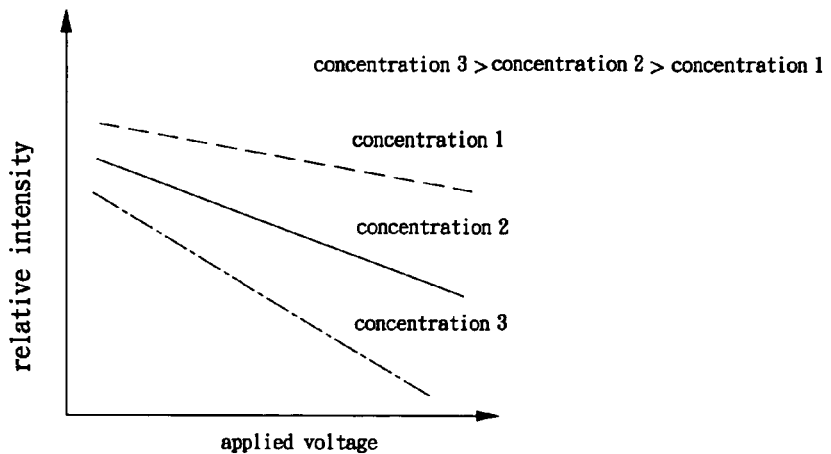
FIG. 4 shows schematically the dependence of relative output intensity on the applied voltage for different analyte concentration.
Figure 5:
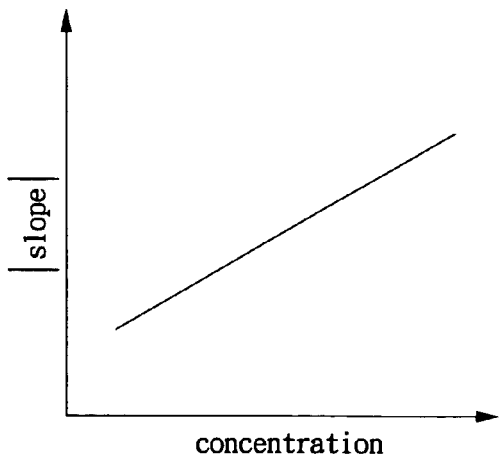
FIG. 5 shows schematically the slopes' absolute value of the corresponding regression straight line as a function of the analyte concentration.

The locations of the minimum in those curves, i.e. the surface plasmon resonance wavelengths $\lambda_{p\ 0}$, $\lambda_{p+}$ and $\lambda_{p-}$, correspond to the wavelength for exciting the surface plasmons. The refractive index of the sensing waveguide 3 increases as the applied voltage V a increases from $-V$ to $+V$. This leads to changes of the condition of surface plasmon resonance, resulting in an increase of the surface plasmon resonance wavelength. As shown in FIG. 3, when a laser with a specific wavelength, $\lambda_0$, which is slightly greater than the surface plasmon resonance wavelength, is used as a source to produce the input wave, the relative intensity $I_-$, $I_0$ and $I_+$ measured at the output ends changes with the applied voltage V a, wherein the changing rate of the relative intensity depends on the dielectric constant of the sample. Taking a solution sample containing bio-chemical materials as an example, in which the dielectric constant is determined by the concentration of the bio-chemical materials therein, the change of the relative intensity versus the applied voltage V a is then determined by that concentration. As shown in FIG. 4, the absolute value of the slope of a regression straight line, which represents the relative intensity as a function of the applied voltage, changes with the concentration, wherein concentration 3 >concentration 2 >concentration 1. As shown in FIG. 5, the absolute value of the slope exhibits a significant increase as the concentration increases. Therefore, an exact determination of the concentration of bio-chemical materials in the sample can be made by taking measurements of the slope of the regression straight line. Furthermore, using a lock-in amplifier can further improve the measurement accuracy, stability, and ability to reduce the noises from background.

The application of a sensing method based on the electro-optical effect in the present invention is generally not restricted. When e.g. applied in characterizing material property an/or concentration of a sample, the sensing method of the present invention comprises: (1) measuring an output intensity versus the applied voltage as a function describing the electro-optical modulation effect, said output intensity can be the relative intensity as shown in FIG. 4; (2) determining a slope of a regression straight line based on said function describing the electro-optical modulation effect, wherein the relation of the slope with the concentration is e.g. shown in FIG. 4 and FIG. 5; (3) determining material property and/or concentration based on said slope, as e.g. shown in FIG. 5.

Therefore, a sensing method and device based on the electro-optical modulation of the present invention show advantages of high accuracy, ability to reduce noises, small volume, easy operation and low cost for building the measuring system. Taking human serum albumin as an example for the material to be detected, it has been confirmed that the present invention can be successfully applied to measure the concentration of beta-blocker (a medicine used against heart diseases).

While the present invention has been illustrated with the preferred embodiment, it will be understood by those skilled in the art that the foregoing and other changes in form and details may be made therein without departing from the spirit and scope of the present invention which should be limited only by the scope of the appended claims.

What is claimed is:

1. A surface-plasmon-resonance sensing method based on the electro-optical modulation, wherein a voltage is applied to modify the condition of surface plasmon resonance, and said method comprising:

putting a sample on a surface plasmon resonance sensing device;

inputting an electromagnetic wave into the surface plasmon resonance sensing device;

applying the voltage on the electrode ends of the surface plasmon resonance sensing device to produce an electric field for electro-optically modulating surface plasmon resonance condition;

using a detector to measure the output intensity of the surface plasmon resonance sensing device;

calculating the relation between the output intensity of the surface plasmon resonance sensing device and said applied voltage, describing the electro-optical modulation effect;

determining the slope of regression straight line according to the relation describing the electro-optical modulation effect;

providing material properties of the sample and/or concentrations therein based on the slope of the regression straight line.

2. A surface-plasmon-resonance sensing device based on the electro-optical modulation, provided on a surface of a substrate, comprising:

a waveguide region, being provided on one side of said substrate, wherein said waveguide region comprises a sensing waveguide, a reference waveguide, an input end and an output end, said sensing waveguide is covered by a metallic layer, said input end is utilized as a common input end at one common end of said sensing waveguide and said reference waveguide, an another end of said reference waveguide is provided as a reference output end, and an another end of said sensing waveguide is provided as a sensing output end of said output end;

an electrode section, providing an applied voltage across two sides of said sensing waveguide to produce an electric field in said sensing waveguide; and a sample, being positioned on said sensing waveguide, wherein a sensing output intensity and a reference output intensity are measured respectively at said sensing output end and said reference output end by using detectors, a relative intensity is determined by dividing said sensing output intensity by said reference output intensity, wherein condition of said surface-plasmon-resonance is modified accordingly to changes of said applied voltage, resulting in a function describing the electro-optical modulation effect in terms of said relative intensity, and said relative intensity changes with said applied voltage, wherein changing rate of said relative intensity with said applied voltage depends on material properties or concentrations of said sample and is equaled to slope of regression straight line of a relation of changes between relative intensity's variation and said applied voltage, wherein, an exact determination of said material properties or said concentrations of said sample is made by firstly taking measurements of said slope of said regression straight line of said relation of changes between said relative intensity's variation and said applied voltage, and then is determined accordingly to calibration data.

3. The sensing device of claim 2, wherein said substrate material exhibits said electro-optical effect, and said waveguide region is provided by locally introducing ions inclusions into said substrate.

4. The sensing device of claim 2, wherein said substrate is a lithium niobate crystal, and said inclusions are titanium and/or other impurities for forming a waveguide structure.

5. The sensing device of claim 2, wherein said material of said metallic layer is a metal to excite surface plasmons by coupling with an electromagnetic wave transmitting in said sensing waveguide.

6. The sensing device of claim 5, wherein said metal is gold, or silver, or other metallic materials that can excite surface plasmons.

7. The sensing device of claim 2, wherein said waveguide region is covered by a separating layer, which comprises an opening at a location corresponding to said sensing waveguide.

8. The sensing device of claim 7, wherein said separating layer is a layer of silicon dioxide or other dielectric materials.

9. The sensing device of claim 2, wherein said electrode section is covered by an isolating layer.

10. The sensing device of claim 9, wherein said isolating layer is a layer of silicon dioxide or other dielectric materials.

* * * * *